United States Patent [19]

Briggs

[11] 4,281,286

[45] Jul. 28, 1981

[54] APPARATUS AND METHOD FOR DETECTING WET AND ICY CONDITIONS ON THE SURFACE OF A PATHWAY

[75] Inventor: Donald E. Briggs, St. Louis County, Mo.

[73] Assignee: Surface Systems, Inc., St. Louis County, Mo.

[21] Appl. No.: 94,556

[22] Filed: Nov. 15, 1979

[51] Int. Cl.³ ............................................. G01R 27/26
[52] U.S. Cl. ................................ 324/61 R; 324/65 R
[58] Field of Search ................. 324/61 R, 65 R, 57 R; 323/65, 67, 68

[56] References Cited

U.S. PATENT DOCUMENTS

| | | |
|---|---|---|
| 2,419,266 | 4/1947 | Kliever et al. |
| 3,241,062 | 3/1966 | Baird .................... 324/61 R |
| 3,243,793 | 3/1966 | Goldman |
| 3,255,411 | 6/1966 | Norwich ............... 324/61 R |
| 3,255,412 | 6/1966 | Liu |
| 3,290,588 | 12/1966 | Norwich ............... 324/61 R |
| 3,323,045 | 5/1967 | Baird .................... 324/61 R |
| 3,323,049 | 5/1967 | Hanken ................. 324/61 R |
| 3,428,890 | 2/1969 | Peck et al. |
| 3,873,927 | 3/1975 | Overall |
| 3,882,381 | 5/1975 | Gregory |
| 3,986,110 | 10/1976 | Overall |
| 4,135,151 | 1/1979 | Rogers et al. |

FOREIGN PATENT DOCUMENTS 2078982 11/1971 France .

Primary Examiner—Stanley T. Krawczewicz
Attorney, Agent, or Firm—Senniger, Powers, Leavitt and Roedel

[57] ABSTRACT

Detection of wet and icy surface conditions on the surface of a pathway is accomplished using a block of electrically insulative material embedded in the pathway with its top surface flush with the surface of the pathway and exposed to atmospheric precipitation. A sensor electrode is encapsulated in the block and is positioned a predetermined distance beneath the top surface of the block so that an accumulation of atmospheric precipitation on the top surface affects the capacitance and conductance between the sensor electrode and the pathway. Provision is made for detecting the presence of impurities such as salt on the block's top surface. A time-varying electrical current is supplied to the sensor electrode at at least two different predetermined frequencies. The apparatus is relatively sensitive to impurities on the block's surface at one of the predetermined frequencies and is relatively insensitive to said impurities at the second predetermined frequency. The frequency of the current supplied to the sensor electrode when substantially pure precipitation is present on the block's top surface is the first predetermined frequency and the frequency of the supplied current is the second predetermined frequency when impurities are detected. The presence of precipitation is signalled when the capacitive and conductive losses between the sensor electrode and the pathway are indicative of such precipitation on the pathway.

25 Claims, 6 Drawing Figures

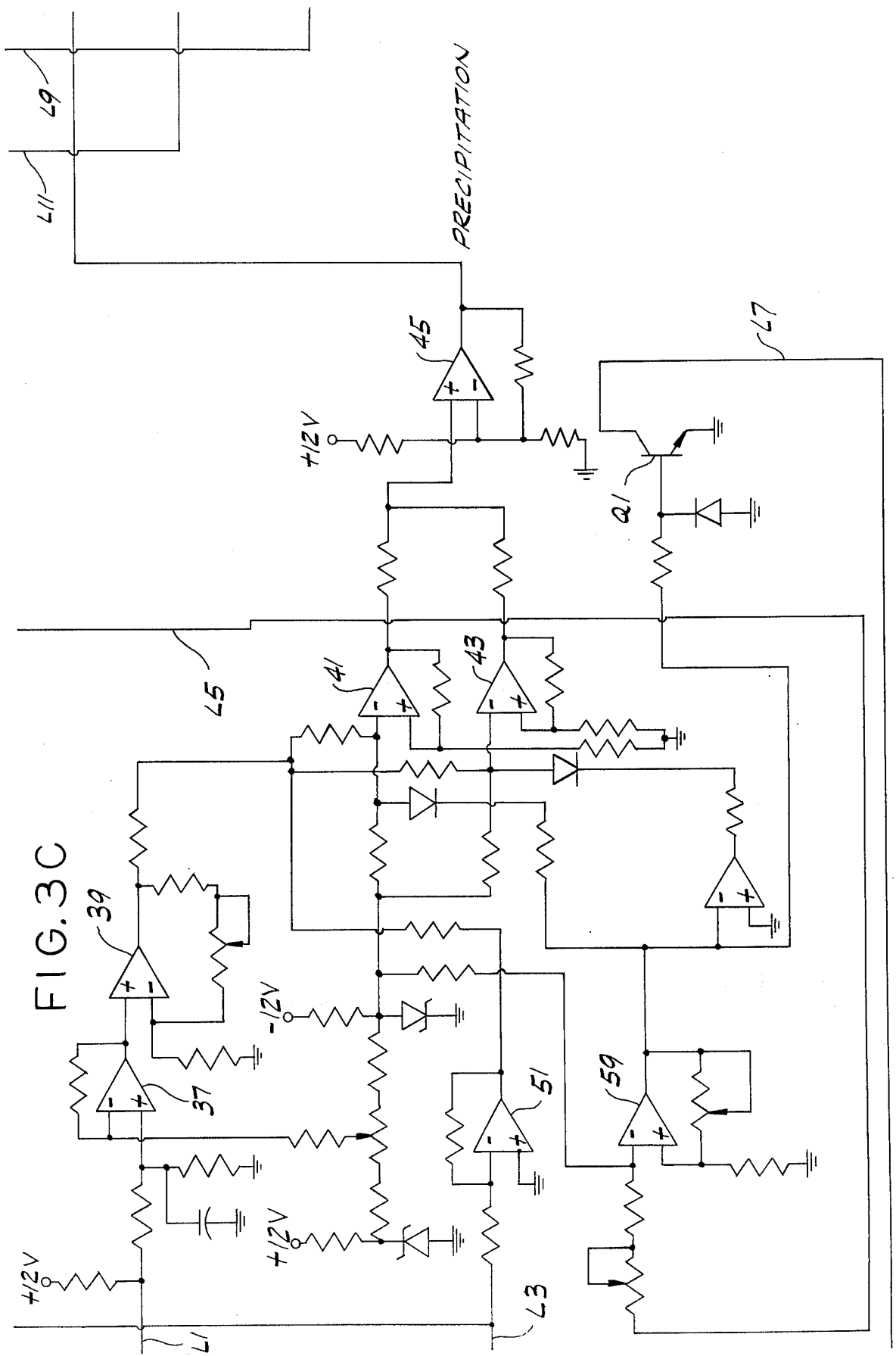

APPARATUS AND METHOD FOR DETECTING WET AND ICY CONDITIONS ON THE SURFACE OF A PATHWAY

BACKGROUND OF THE INVENTION

This invention relates to precipitation detectors and particularly to apparatus and method for detecting wet and icy conditions on the surface of a pathway, such as a highway or airport runway.

Apparatus which detect wet and icy surface conditions are of tremendous aid to motorists, highway departments, airport managers, and the like. Several such systems have been proposed, including those disclosed in coassigned U.S. Pat. Nos. 3,873,927, 3,882,381 and 4,135,151. Other patents in the field include U.S. Pat. Nos. 2,419,266, 3,243,793 and 3,428,890, and French Pat. No. 2,078,982.

While prior systems provide useful information on surface conditions, it would be advantageous if their effectiveness could be improved in certain respects. For example, it has been found that the system of U.S. Pat. No. 4,135,151 is so sensitive to impurities such as salt or the like on the surface of the sensor block when the apparatus is operated at a frequency of 5 KHz that moisture is detected when the surrounding pathway is dry. Prior systems, which operate at substantially higher frequencies, e.g., 200 KHz, are not this sensitive to impurities but are also not as sensitive to pure water on the surface of the sensor block. Operation at these higher frequencies can result in pure water going undetected. In addition, the response of prior systems is frequently subject to drift and variation as a function of temperature.

SUMMARY OF THE INVENTION

Among the several objects of the present invention may be noted the provision of an apparatus and method which reliably and accurately detects wet and icy conditions on the surface of a pathway; the provision of such apparatus which functions accurately in the presence of impurities on the pathway; the provision of such apparatus which functions accurately to detect pure water or ice on the pathway; and the provision of such apparatus which accurately and reliably detects precipitation over wide variations in ambient temperature. Other objects and features will be in part apparent and in part pointed out hereinafter.

Briefly, apparatus of the present invention includes a block of electrically insulative material adapted to be embedded in a pathway with the top surface of the block substantially flush with the surface of the pathway and exposed to atmospheric precipitation. A sensor electrode is encapsulated in the block and positioned a predetermined distance beneath the top surface of the block so that an accumulation of atmospheric precipitation on the top surface affects the capacitance and conductance between the sensor electrode and the pathway. The apparatus also includes circuitry for detecting the presence of predetermined concentrations of impurities such as salt or the like on the top surface of the block and circuitry for supplying a time-varying electrical current to the sensor at at least two different predetermined frequencies, the apparatus being relatively sensitive to impurities on the surface of the block at one of the predetermined frequencies and being relatively insensitive to said impurities at another of the predetermined frequencies. Additional circuitry, responsive to the detecting circuitry, controls the current supplying circuitry to supply electrical current to the sensor electrode at the one predetermined frequency when substantially pure precipitation is present on the top surface of the block and at the other predetermined frequency when impurities are detected. Precipitation signal circuitry is connected to the sensor electrode for signalling the presence of atmospheric precipitation on the pathway, the precipitation signal circuitry being responsive to the capacitive and conductive losses between the sensor electrode and the pathway when precipitation is present on the pathway to signal the presence of the precipitation.

The method of the present invention includes embedding a block of electrically insulative material in the pathway with the top surface of the block substantially flush with the surface of the pathway and exposed to atmospheric precipitation, the block having a sensor electrode encapsulated therein, the sensor electrode being positioned a predetermined distance beneath the top surface of the block so that an accumulation of atmospheric precipitation on the top surface affects the capacitance and conductance between the sensor electrode and the pathway. The method further includes detecting the presence of predetermined concentrations of impurities such as salt or the like on the top surface of the block, supplying a time-varying electrical current to the sensor electrode, and examining whether the capacitive and conductive losses between the sensor electrode and the pathway exceed a predetermined amount indicative of the presence of atmospheric precipitation on the pathway. When impurities are not detected on the top surface of the block, the time-varying current has a first predetermined frequency and when impurities are detected the time-varying current has a second predetermined frequency.

BRIEF DESCRIPTION OF THE DRAWINGS

FIGS. 3A-3D are schematics of the electrical circuitry used with the sensing apparatus shown in FIGS. 1 and 2.

Corresponding reference characters indicate corresponding parts throughout the several views of the drawings.

DESCRIPTION OF A PREFERRED EMBODIMENT

Figure 1:
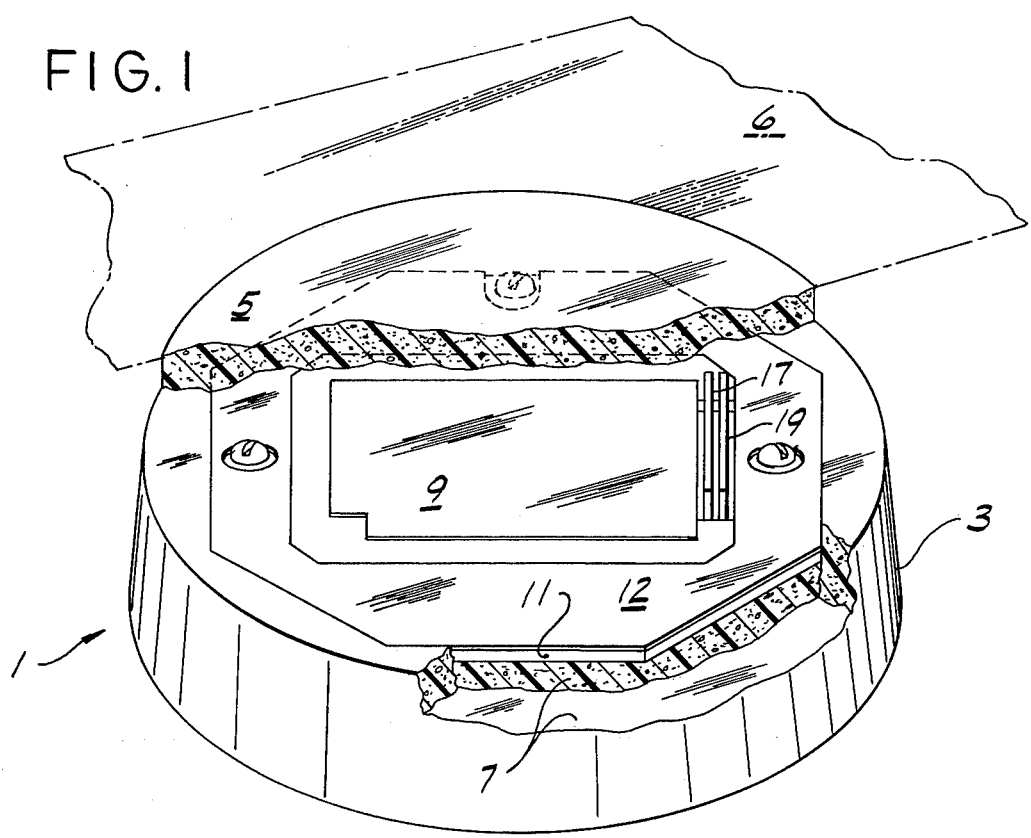
FIG. 1 is a perspective view of sensing apparatus of the present invention with parts broken away for clarity.

Referring now to the drawings, apparatus of this invention for detecting wet and icy conditions on the surface of a pathway includes a sensor indicated generally at 1. Sensor 1 includes a block 3 of electrically insulative material having a generally flat top surface 5. Block 3 is embedded in a pathway, such as an airport runway or the surface of a bridge, with its top surface 5 being positioned so it is substantially flush with the surface of the pathway. In this position, top surface 5 is exposed to the atmospheric precipitation, i.e., rain, sleet, snow, etc., which falls on the surrounding pathway. Top surface 5 is also, of course, exposed to any impurities such as salt and the like which might be present on the pathway. A typical pathway is indicated by phantom lines 6 in FIG. 1. The electrically insulative material making up block 3 includes a thermosetting synthetic resin material 7 having a dielectric constant which is relatively independent of temperature.

Figure 2:
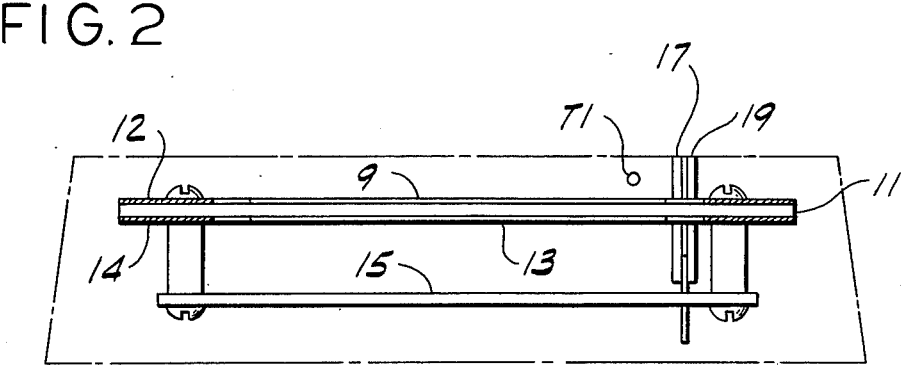
FIG. 2 is an elevation of the interior of sensing apparatus of the present invention with the outline shown only in phantom and with parts broken away to reveal interior detail.
Figure 3A:
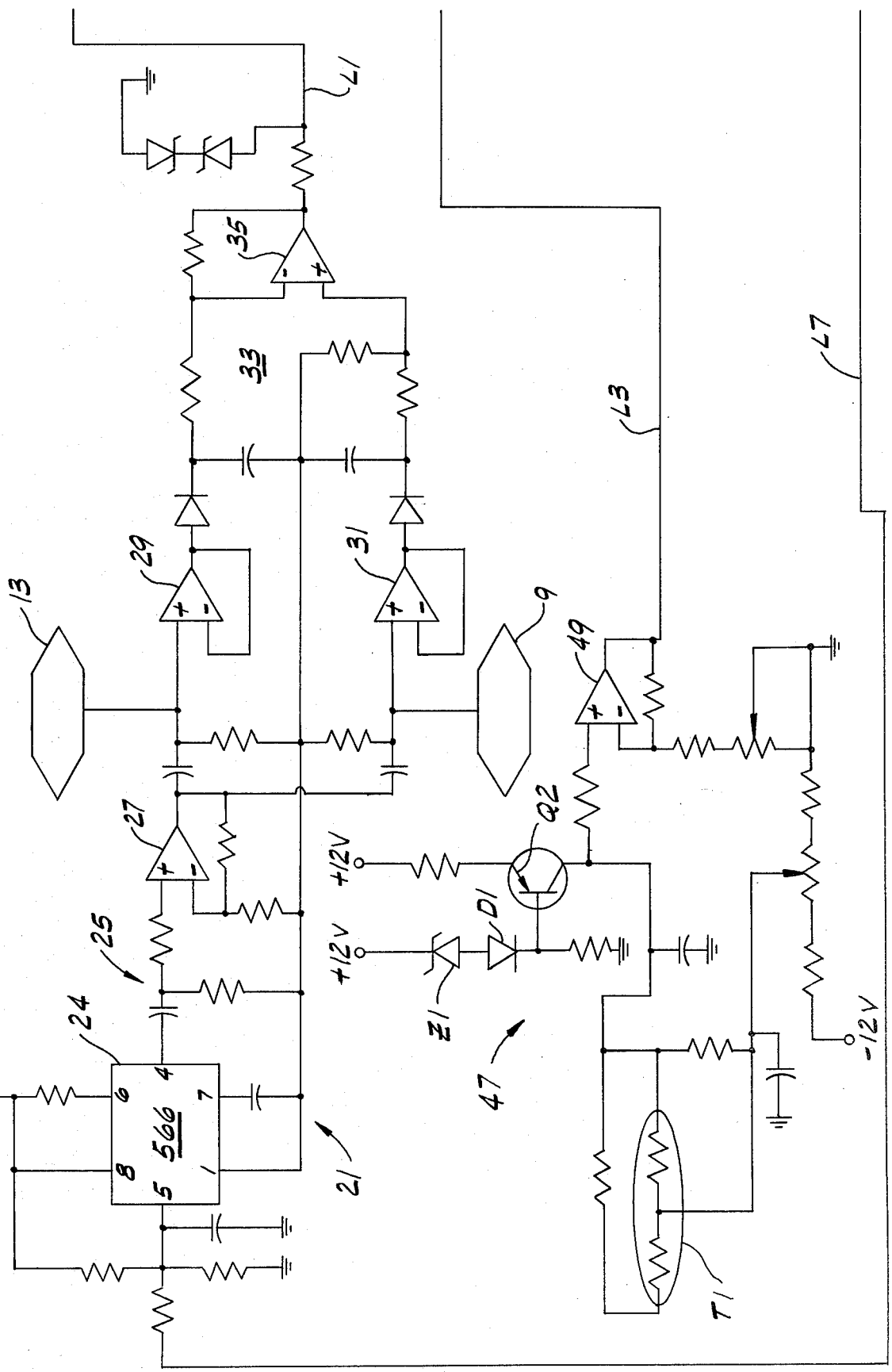
Figure 3B:
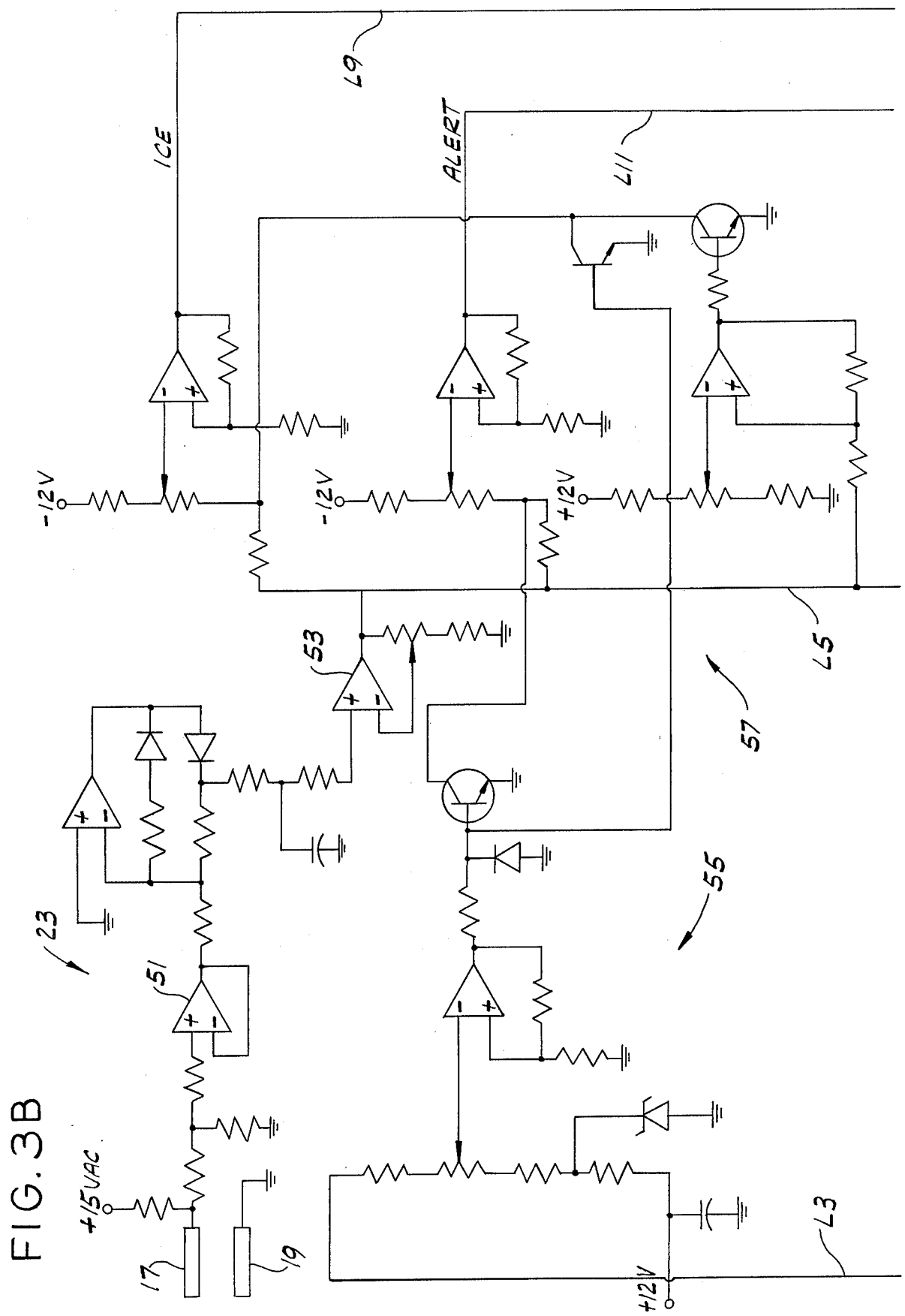

A large, generally rectangular sensor electrode 9 is encapsulated in block 3 and positioned a predetermined distance, on the order of one-quarter inch, beneath top surface 5 of block 3. Electrode 9 is a metallic foil material bonded to the top surface of a substrate material 11, which substrate typically is an insulating board suitable for use in making printed circuit boards, said substrate itself being encapsulated in block 3. Bonded to the bottom surface of substrate 11 is a second electrode 13 (see FIG. 2). Substrate 11 is approximately three-sixteenths of an inch thick and maintains electrodes 9 and 13 substantially parallel to each other. Surrounding electrodes 9 and 13, but insulated therefrom, are two grounded electrodes 12 and 14, also bonded to the top and bottom, respectively, of substrate 11. Mounted below substrate 11 and spaced therefrom about one-half inch is a printed circuit board 15 to which various of the electronic components shown in FIGS. 3A–3C are connected. These components are not shown in FIG. 2 since their inclusion would tend to obscure the relationship between substrate 11 and printed circuit board 15. Also shown in FIG. 2 are a pair of conductors, specifically a pair of parallel plates 17 and 19, whose top portions are exposed on top surface 5 of block 3.

Referring to FIG. 3A there is shown generally at 21 means for supplying a time-varying electrical current to sensor electrode 9 and in particular for supplying said time-varying current at a first predetermined frequency, such as a frequency within the range of from approximately 500 Hz to approximately 10 KHz, or at a second predetermined frequency, such as a frequency within the range of from approximately 50 KHz to approximately 300 KHz. It is preferred that the first predetermined frequency is approximately 5 KHz and that the second predetermined frequency be approximately 150 KHz.

The reason for using two different frequencies is as follows: Sensor 1 operates substantially in the same manner as the sensor disclosed in coassigned U.S. Pat. No. 4,135,151. Some of the current supplied to electrode 9 is lost, i.e., shunted to ground, due to capacitive and conductive effects between that electrode and pathway 6, the amount shunted being generally a function of whether there is atmospheric precipitation on top surface 5. The capacitance between top surface 5 and pathway 6, on the one hand, and electrode 9, on the other, is quite small when top surface 5 is dry and the conductance is virtually zero, resulting in practically no shunting of current from electrode 9 to pathway 6 in dry weather. When there is precipitation on surface 5, however, there is a substantial shunting of current between the electrode and the pathway. In certain situations, such as when impurities such as salt are present on the top surface of block 3, the sensor of the aforesaid U.S. Patent can register the presence of water even when the surrounding pathway is dry. This is because the sensor of that patent is extremely sensitive to moisture and to the aforesaid impurities, especially salt. It is possible to reduce the sensitivity to impurities of a sensor such as that disclosed in the aforesaid patent by increasing the frequency of the current supplied to the sensor electrode from roughly 5 KHz, or some other value generally between 500 Hz and 10 KHz, to a somewhat higher frequency generally in the range of from 50 KHz to 300 KHz. However, at these higher frequencies, the sensitivity of such sensors to pure water or ice is so reduced that the sensor might not detect the presence of such pure precipitation. Thus, it has been found to be desirable to operate at two different frequencies—one to be used when impurities are present on the top surface of block 3 and one to be used when the impurities are absent.

Turning now to FIG. 3B, means are shown generally at 23 for detecting the presence of impurities on the top surface of block 3, and particularly for detecting predetermined concentrations of such impurities, the predetermined concentrations being the impurity amounts that cause unreliable operation at the lower predetermined frequency. The detecting means includes parallel plates 17 and 19, a portion of each of which are exposed to the atmosphere and hence to any impurities which might be present on the top surface of block 3.

Figure 3D:
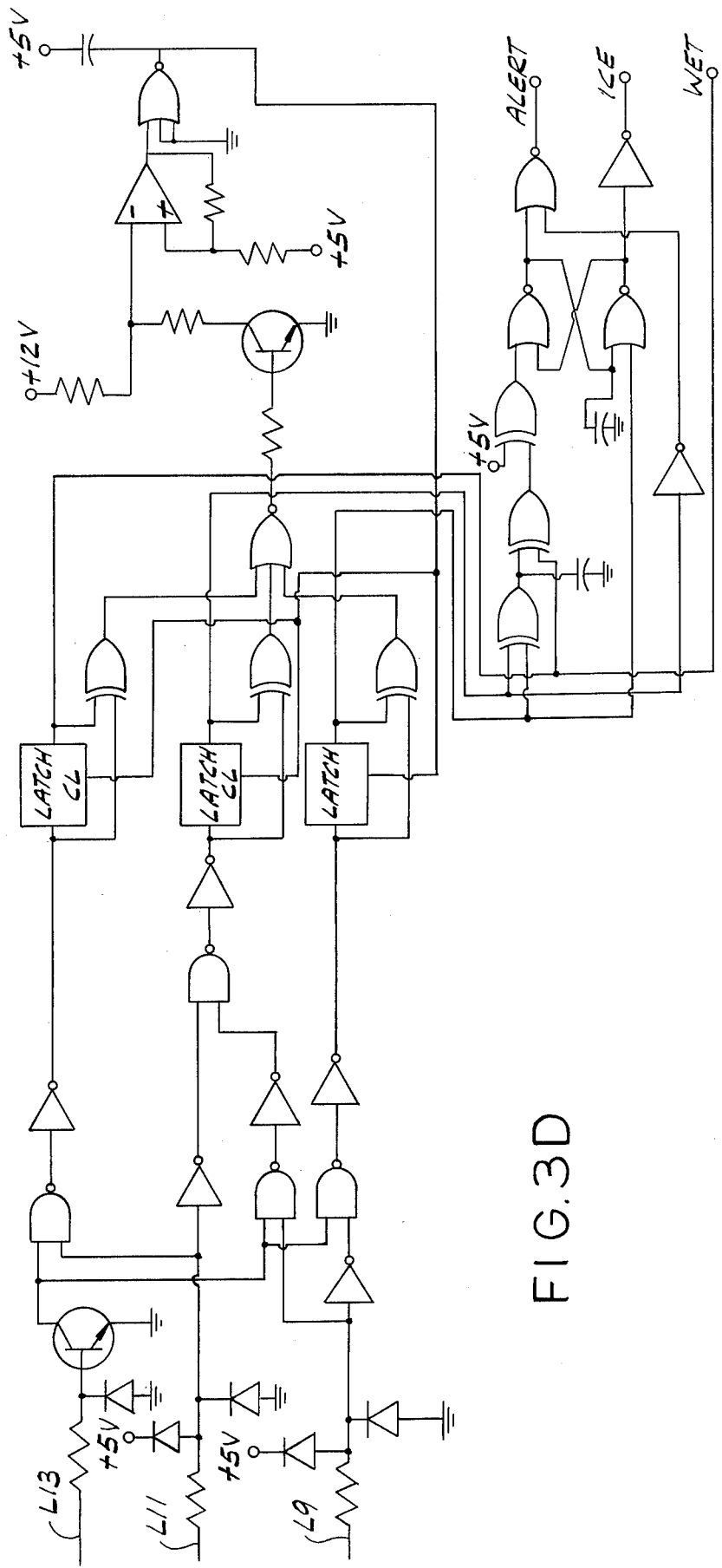

Current-supplying means 21 is controlled by a transistor Q1 (see FIG. 3C), which transistor, as is explained below, is responsive to detecting means 23. That is, transistor Q1 constitutes means for controlling time-varying current supplying means 21 to supply electrical current to the sensor electrode at the first predetermined frequency when substantially pure precipitation is present on the top surface of the block and at the other predetermined frequency when impurities are detected. Also shown on FIG. 3C, and on FIG. 3D, is circuitry constituting precipitation signal means for signalling the presence of atmospheric precipitation on pathway 6, said precipitation signal means being responsive to the capacitive and conductive losses between electrode 9 and pathway 6 when precipitation is present on the pathway to signal the presence of the precipitation.

Considering the electrical schematic of the circuitry of the present invention in more detail, there is shown in FIG. 3A a Signetics type SE 566 function generator 24 having a voltage sensitive control terminal (pin 5) which in operation generates a triangle wave of either the first or second predetermined frequency, as required, and supplies its output through a waveshaping network 25 to an operational amplifier (op amp) 27. The operational amplifier in turn supplies its output, which generally resembles (for example) a truncated sine wave, to sensor electrode 9 and to second electrode 13. Thus, op amp 27 and the resistor-capacitor networks associated with its output constitute means for supplying substantially the same current waveforms to electrodes 9 and 13. As is explained above, if atmospheric precipitation is present on the top surface of block 3, there will be capacitive and conductive losses between electrode 9 and the pathway and the current beyond that point in the circuit will be reduced from the value it would have were the surface dry.

The reason the output of op amp 27 is also supplied to electrode 13 is in part to provide temperature compensation and in part to compensate for the difference in response of the system at the different operating frequencies. Although the material of which block 3 is composed is chosen to minimize the change in dielectric constant due to temperature changes, this does not completely eliminate all such drift. The use of electrode 13 makes a substantial improvement in the temperature response of the system. Since sensor electrode 9 and electrode 13 are both encapsulated in the same dielectric medium and are both at substantially the same temperature, the dielectric constant of the surrounding material will be substantially the same for both electrodes. Thus, the response of electrode 13 to the time-varying current supplied from means 21 can be used as a standard against which to measure the response of sensor electrode 9. This is particularly true since electrode 13, being farther from the top surface of block 3 than is sensor electrode 9, has a response to the signal from op amp 27 which is relatively unaffected by the presence or absence of moisture on the top surface of the block since it has substantially smaller capacitive and conductive losses between it and the pathway than those between electrode 9 and the pathway. In a similar manner electrode 13 is used to compensate for differences in response of the system at different frequencies. Because the sensor of the present invention uses capacitive effects to detect the presence of moisture on pathway 6, the response of the system naturally changes when the frequency of the signal from op amp 27 is changed. However, this change will be substantially the same for both sensor electrode 9 and for electrode 13. Thus, the response of electrode 13 again is used as a standard against which to compare the response of sensor electrode 9 to determine whether moisture is present on the pathway.

After the signal from op amp 27 is attenuated by sensor electrode 9 and, to a lesser degree, by electrode 13, the resulting signals are supplied through two op amps 29 and 31 and a rectifying and filtering network 33 to another op amp 35 which compares the signals from op amps 29 and 31, and, therefore, constitutes means for comparing the signals from op amps 29 and 31, the difference between those signals being indicative of the presence (or the absence) of atmospheric precipitation on pathway 6. It should be appreciated that the magnitude of the output of op amp 35 is a function of whether or not precipitation is present on the top surface of block 3. This output is supplied via a line L1 to an op amp 37 and an op amp 39, which amplify and scale that output. The output of op amp 39 is supplied to a pair of op amps 41 and 43 which compare that output to a predetermined threshold value which, when exceeded, indicates the presence of precipitation on the pathway. When precipitation is detected at the second predetermined frequency, op amp 41 makes the comparison, while op amp 43 makes the comparison at the first predetermined frequency. The output of op amps 41 and 43 are supplied to an op amp 45 to generate an output signal indicative of the presence of atmospheric precipitation on top surface 5 of the block. Thus, op amp 45, and the circuitry of FIG. 3D, constitute means connected, albeit indirectly, to the sensor electrode for signalling the presence of atmospheric precipitation on pathway 6, which means are responsive to the capacitive and conductive losses between the sensor electrode and the pathway when precipitation is present on the pathway to signal the presence of the precipitation.

It has been found to be desirable to provide even more temperature compensation in the present system than that provided by electrode 13. This is accomplished by means of a temperature compensating circuit 47, which constitutes means for sensing the temperature of the pathway, said circuit comprising a Zener diode Z1 and a diode D1 connected to the base of a p-n-p transistor Q2, a thermistor T1, and an op amp 49. The voltage measured at the collector of transistor Q2 is a function of the resistance of thermistor T1. Since thermistor T1 has a negative temperature coefficient of resistance, the output of op amp 49 varies inversely with temperature. This output is supplied via a line L3 to another op amp 51 (see FIG. 3C) which in turn supplies the temperature dependent signal to op amps 41 and 43, discussed above. It is preferred that thermistor T1 be physically located in block 3 and particularly, that it be disposed a short distance above sensor electrode 9 as is shown in FIG. 2.

Referring now to the top of FIG. 3B, plate 17 is shown connected to a fifteen to seventeen-volt, sixty-cycle alternating current source and plate 19 is shown connected to ground. Since plates 17 and 19 are exposed to atmospheric precipitation and to any impurities present on the top surface of the sensor, the resistance between them is affected by that precipitation and impurities. As is explained in the aforesaid U.S. Pat. No. 4,135,151, the resistance between the plates is greater when the precipitation is ice than when it is water. In addition the resistance between them is less when impurities are present. Thus, the plates can serve not only to indicate the presence of ice but also to indicate the presence of impurities. When the resistance between the plates is relatively low, a relatively large amount of the current from the AC source is shunted to ground, whereas when the resistance is relatively high little current will be shunted. This affects the voltage present at the input of an op amp 51, so that the output of that op amp is a function of the resistance, or conversely of the conductivity, between plates 17 and 19. That is, the alternating current source and op amp 51 constitute means for testing the conductivity between plates 17 and 19. This output is rectified and filtered and supplied to an op amp 53. There is also shown on FIG. 3B circuitry 55 which receives a signal supplied from temperature compensating circuit 47. That signal and the circuitry that supplies it, in a slightly modified form, are described in detail in U.S. Pat. No. 4,135,151 and that description will not be repeated here. Briefly, this circuitry 55 ensures that there will not be an erroneous indication that ice is present between plates 17 and 19 when the temperature is above 33° F. (0.56° C.). The output of op amp 53 and the outputs of circuitry 55 are supplied to a decoding circuit 57, which again closely resembles a circuit which is described in detail in the aforementioned U.S. patent. Circuit 57 has two outputs, indicating ice on the pathway and an alert condition respectively.

The output of op amp 53 is also supplied via a line L5 to an op amp 59 (see FIG. 3C) which is configured so as to turn transistor Q1 on and off as required by the absence or presence of impurities on the surface of block 3. Thus, op amps 53 and 59, with their associated resistor networks, constitute means for signalling the presence of impurities on pathway 6 if the conductivity between plates 17 and 19 has a value indicative of the presence of impurities. When transistor Q1 is conducting, it pulls the voltage at control pin 5 of the function generator down somewhat and the resulting output of the generator has a frequency of, for example, 150 KHz. On the other hand, when transistor Q1 is not conducting, the voltage at control pin 5 is somewhat higher and the output of the generator is at a frequency of, for example, 5 KHz. The actual value of the frequencies will be determined by the values of the resistors in the network connected to pin 5. Thus, transistor Q1 constitutes means responsive to a signal from detecting means 23 indicating the presence of impurities on pathway 6 to change a control voltage supplied to the current supplying means.

The signals indicating ice and an alert condition are supplied via lines L9 and L11 to the circuitry of FIG. 3D, and the signal from op amp 45 indicating the presence or absence of precipitation is supplied to that same circuitry via a line L13. The circuitry of FIG. 3D is substantially the same as the corresponding circuitry disclosed in U.S. Pat. No. 4,135,151 and hence it will not be described in detail here. Briefly, however, this circuitry decodes the signals on lines L9, L11, and L13 and produces a system output indicating a wet condition, an icy condition, or an alert condition.

In view of the above, it will be seen that the several objects of the invention are achieved and other advantageous results attained.

As various changes could be made in the above products and methods without departing from the scope of the invention, it is intended that all matter contained in the above description or shown in the accompanying drawings shall be interpreted as illustrative and not in a limiting sense.

What is claimed is:

1. Apparatus for detecting wet and icy conditions on the surface of a pathway, comprising:
   a block of electrically insulative material adapted to be embedded in the pathway with the top surface of the block substantially flush with the surface of the pathway and exposed to atmospheric precipitation;
   a sensor electrode encapsulated in said block and positioned a predetermined distance beneath the top surface of the block so that an accumulation of atmospheric precipitation on said top surface affects the capacitance and conductance between the sensor electrode and the pathway;
   means for detecting the presence of predetermined concentrations of impurities such as salt or the like on the top surface of the block;
   means for supplying a time-varying electrical current to the sensor electrode at at least two different predetermined frequencies, the apparatus being relatively sensitive to impurities on the surface of the block at one of the predetermined frequencies and being relatively insensitive to said impurities at the second predetermined frequency;
   means, responsive to the detecting means, for controlling the current supplying means to supply electrical current to the sensor electrode at the one predetermined frequency when substantially pure precipitation is present on the top surface of the block and at the other predetermined frequency when impurities are detected; and
   precipitation signal means connected to the sensor electrode for signalling the presence of atmospheric precipitation on the pathway, said precipitation signal means being responsive to the capacitive and conductive losses between the sensor electrode and the pathway when precipitation is present on the pathway to signal the presence of said precipitation.

2. Apparatus as set forth in claim 1 wherein the impurity detecting means includes a pair of conductors having portions thereof exposed to the atmosphere and exposed to any impurities present on the pathway.

3. Apparatus as set forth in claim 2 wherein the detecting means further includes means for testing the conductivity between the pair of electrodes and means for signalling the presence of impurities on the pathway if the conductivity has a value indicative of the presence of said impurities on the pathway.

4. Apparatus as set forth in claim 3 wherein the controlling means is responsive to the signal from the detecting means indicating the presence of impurities on the pathway to change a control voltage supplied to the current supplying means.

5. Apparatus as set forth in claim 4 wherein the current supplying means includes a function generator having a voltage sensitive control terminal, said control voltage being applied to the control terminal to govern the frequency of the current supplied to the sensor electrode.

6. Apparatus as set forth in claim 1 wherein the impurity detecting means includes means for testing the conductivity of precipitation on the pathway and for signalling the presence of impurities on the pathway if the conductivity has a value indicative of the presence of said impurities on the pathway.

7. Apparatus as set forth in claim 1 wherein the current supplying means includes a function generator.

8. Apparatus as set forth in claim 7 wherein the output of the function generator is supplied to the sensor electrode and the frequency of the output of the function generator is controlled by the controlling means.

9. Apparatus as set forth in claim 1 further including a second electrode encapsulated in said block and positioned farther than the sensor electrode from the top surface of the block, said second electrode being connected to the current supplying means, whereby the capacitive and conductive losses between the second electrode and the pathway are substantially less than the capacitive and conductive losses between the first electrode and the pathway.

10. Apparatus as set forth in claim 9 wherein the second electrode and the sensor electrode are parallel and substantially identical and wherein the current supplying means includes means for supplying substantially the same current waveforms to the second and sensor electrodes.

11. Apparatus as set forth in claim 10 further including means for generating first and second electrical signals which signals are a function of the capacitive and conductive losses resulting from supplying the time-varying electrical current to the sensor electrode and second electrode respectively, and means for comparing the first and second electrical signals, the difference between said first and second signals being indicative of the presence of atmospheric precipitation on the pathway.

12. Apparatus as set forth in claim 1 further including means for sensing the temperature of the pathway.

13. Apparatus as set forth in claim 12 wherein the temperature sensing means includes a thermistor encapsulated in said block.

14. Apparatus as set forth in claim 13 wherein the thermistor is disposed closer than the sensor electrode to the top surface of the block.

15. Apparatus as set forth in claim 1 wherein the time-varying current supplying means includes means for supplying current at a first predetermined frequency selected in the range of from approximately 500 Hz to approximately 10 KHz.

16. Apparatus as set forth in claim 15 wherein the time-varying current supplying means includes means for supplying current at a first predetermined frequency of approximately 5 KHz.

17. Apparatus as set forth in claim 1 wherein the time-varying current supplying means includes means for supplying current at a second predetermined frequency selected in the range of from approximately 50 KHz to approximately 300 KHz.

18. Apparatus as set forth in claim 17 wherein the time-varying current supplying means includes means for supplying current at a second predetermined frequency of approximately 150 KHz.

19. The method of detecting wet and icy conditions on the surface of a pathway comprising:

embedding a block of electrically insulative material in the pathway with the top surface of the block substantially flush with the surface of the pathway and exposed to atmospheric precipitation, said block having a sensor electrode encapsulated therein, said sensor electrode being positioned a predetermined distance beneath the top surface of the block so that an accumulation of atmospheric precipitation on said top surface affects the capacitance and conductance between the sensor electrode and the pathway;

detecting the presence of predetermined concentrations of impurities such as salt or the like on the top surface of the block;

supplying a time-varying electrical current having a first predetermined frequency to the sensor electrode when impurities are not detected on the top surface of the block and supplying a time-varying electrical current having a second predetermined frequency to the sensor electrode when impurities are detected; and determining whether the capacitive and conductive losses between the sensor and the pathway exceed a predetermined amount indicative of the presence of atmospheric precipitation on the pathway.

20. The method of claim 19 wherein the first predetermined frequency is substantially no greater than 10 KHz.

21. The method of claim 20 wherein the first predetermined frequency is approximately 5 KHz.

22. The method of claim 19 wherein the first predetermined frequency is substantially no less than 500 Hz.

23. The method of claim 19 wherein the second predetermined frequency is substantially no greater than 300 KHz.

24. The method of claim 23 wherein the second predetermined frequency is approximately 150 KHz.

25. The method of claim 19 wherein the second predetermined frequency is substantially no less than 50 KHz.

* * * * *